(12) United States Patent
Konno et al.

(10) Patent No.: US 11,107,259 B2
(45) Date of Patent: Aug. 31, 2021

(54) INFORMATION TERMINAL, BIOLOGICAL INFORMATION MANAGEMENT METHOD, BIOLOGICAL INFORMATION MANAGEMENT PROGRAM AND COMPUTER-READABLE STORAGE MEDIUM

(71) Applicant: NIHON KOHDEN CORPORATION, Tokorozawa (JP)

(72) Inventors: Norihito Konno, Tokyo (JP); Junichi Mogi, Tokyo (JP)

(73) Assignee: Nihon Kohden Corporation, Tokorozawa (JP)

( * ) Notice: Subject to any disclaimer, the term of this patent is extended or adjusted under 35 U.S.C. 154(b) by 0 days.

(21) Appl. No.: 16/360,794

(22) Filed: Mar. 21, 2019

(65) Prior Publication Data

US 2019/0295714 A1 Sep. 26, 2019

(30) Foreign Application Priority Data

Mar. 23, 2018 (JP) .............................. JP2018-056592

(51) Int. Cl.
| | |
|---|---|
| *G06T 11/20* | (2006.01) |
| *G16H 40/63* | (2018.01) |
| *G06F 3/0488* | (2013.01) |
| *H04Q 9/02* | (2006.01) |
| *A61B 5/0205* | (2006.01) |

(Continued)

(52) U.S. Cl.
CPC ........ *G06T 11/206* (2013.01); *A61B 5/02055* (2013.01); *A61B 5/14542* (2013.01); *A61B 5/339* (2021.01); *A61B 5/369* (2021.01); *A61B 5/389* (2021.01); *A61B 5/7435* (2013.01); *G06F 3/04883* (2013.01); *G16H 40/63* (2018.01); *H04Q 9/02* (2013.01); *A61B 5/021* (2013.01);

(Continued)

(58) Field of Classification Search
CPC .... G06F 3/048; G06F 3/04883; G06T 11/206; G16H 10/60; A61B 5/0205; A61B 5/021; A61B 5/044; A61B 5/0476; A61B 5/082; A61B 5/14542; A61B 5/742; A61B 5/743
See application file for complete search history.

(56) References Cited

U.S. PATENT DOCUMENTS

| | | | | |
|---|---|---|---|---|
| 8,499,236 B1* | 7/2013 | Keljo | ...................... | G06T 11/60 715/249 |
| 2003/0090524 A1* | 5/2003 | Segerberg | .......... | H04N 21/4314 715/786 |

(Continued)

OTHER PUBLICATIONS

Admin3, "aCalendar+ Calendar & Tasks Android App Review", Nov. 11, 2015, http://bestapps.com/acalendar-calendar-tasks-android-app-review/ (Year: 2015).*

(Continued)

*Primary Examiner* — Michelle L Sams
(74) *Attorney, Agent, or Firm* — Dorsey & Whitney LLP

(57) ABSTRACT

To increase convenience of centralized management of biological information acquired from plural subjects. A wireless communication device receives plural sensor signals corresponding to biological information of plural subjects. A display displays biological information of the subject in a display area generated for each subject based on association between plural subjects and plural sensor signals.

14 Claims, 8 Drawing Sheets

(51) Int. Cl.
*A61B 5/145* (2006.01)
*A61B 5/00* (2006.01)
*A61B 5/339* (2021.01)
*A61B 5/369* (2021.01)
*A61B 5/389* (2021.01)
*A61B 5/08* (2006.01)
*G01S 11/06* (2006.01)
*A61B 5/021* (2006.01)

(52) U.S. Cl.
CPC ............... *A61B 5/082* (2013.01); *G01S 11/06* (2013.01); *H04Q 2209/40* (2013.01)

(56) References Cited

U.S. PATENT DOCUMENTS

| | | | | |
|---|---|---|---|---|
| 2008/0001735 | A1* | 1/2008 | Tran | G06F 19/00 340/539.22 |
| 2011/0010193 | A1* | 1/2011 | Zheng | G16H 40/63 705/2 |
| 2015/0119653 | A1* | 4/2015 | Wake | G06F 19/325 600/301 |
| 2015/0302150 | A1* | 10/2015 | Mazar | G06Q 10/10 705/2 |
| 2016/0110047 | A1* | 4/2016 | Yoon | G06F 3/0482 715/784 |

OTHER PUBLICATIONS

"ACalendar+ Calendar & Tasks", Dec. 16, 2016, https://web.archive.org/web/20161220085600/https://acalendar-android-calendar.soft112.com/ (Year: 2016).*

PhoneSavvyInc, "aCalendar—App Review—Best Calendar for Android", Nov. 5, 2013, https://www.youtube.com/watch?v=XMKz1deDm5I&list=PLk63XNvScvY_sx--jZmt9ZNgBNgCjt1ri&index=2&t=0s (Year: 2013).*

Kim, Jaewon et al., "Pagination versus Scrolling in Mobile Web Search", Proceedings of the 25th ACM International on Conference on Information and Knowledge Management (CIKM '16). 2016. p. 751-760. DOI:https://doi.org/10.1145/2983323.2983720 (Year: 2016).*

* cited by examiner

FIG. 3

| SENSOR ID | SUBJECT ID |
|---|---|
| E003 | P028 |
| E034 | P075 |
| E098 | P223 |
| S001 | P075 |
| S076 | P028 |
| S487 | P223 |
| R072 | P028 |

FIG. 4A
FIG. 4B
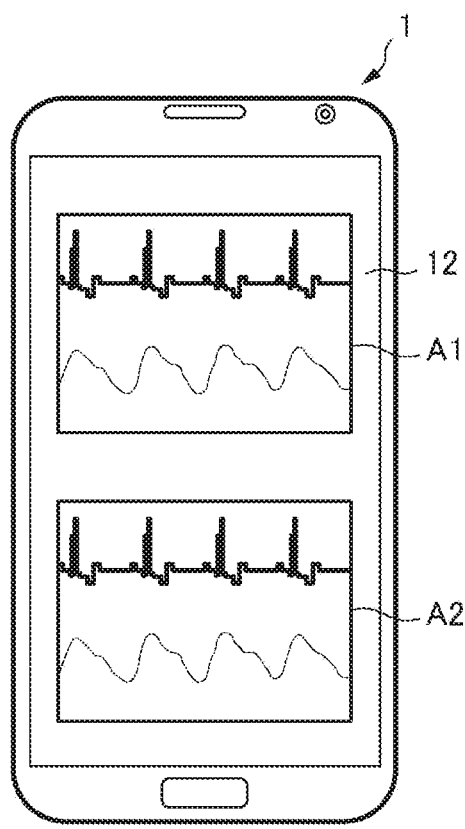
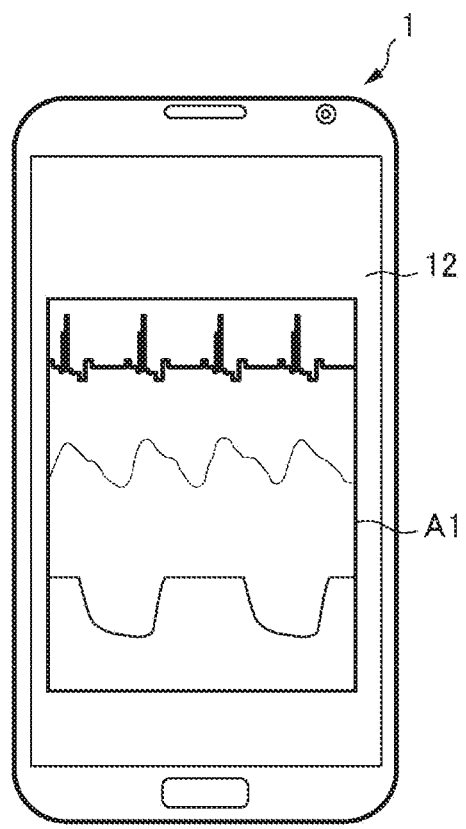

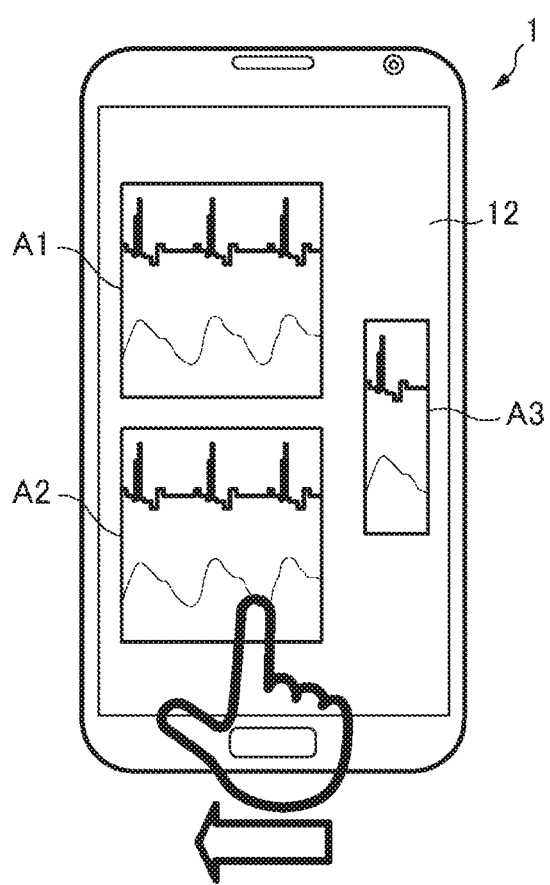
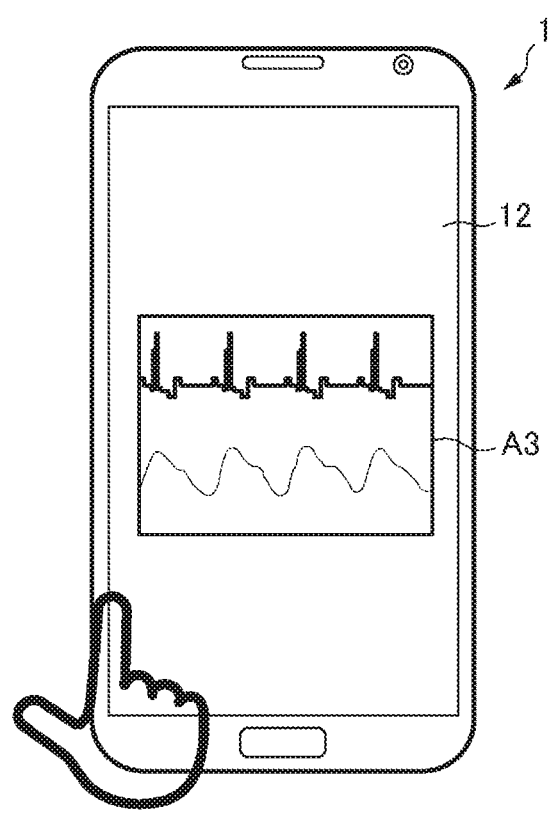
FIG. 5A
FIG. 5B

INFORMATION TERMINAL, BIOLOGICAL INFORMATION MANAGEMENT METHOD, BIOLOGICAL INFORMATION MANAGEMENT PROGRAM AND COMPUTER-READABLE STORAGE MEDIUM

CROSS-REFERENCE TO RELATED APPLICATION(S)

This application claims priority to and the benefit under 35 U.S.C. § 119(a) of the earlier filing date of Japanese Application No. JP 2018-056592 filed Mar. 23, 2018 which is incorporated herein by reference, in its entirety, for any purpose.

BACKGROUND OF THE INVENTION

Field of the Invention

The present disclosure relates to an information terminal and a biological information management method for managing biological information of subjects, a biological information management program allowing the information terminal to execute the biological information management method and a computer-readable storage medium storing the biological information management program.

Description of Related Art

JP-A-2015-084876 (Patent literature 1) discloses a central monitor. The central monitor is an apparatus for performing centralized management of biological information acquired from plural subjects.

SUMMARY OF THE INVENTION

An object of the present disclosure is to increase convenience in centralized management of the biological information acquired from plural subjects.

As one aspect for achieving the above object, there is proposed an information terminal including a wireless communication device receiving plural sensor signals corresponding to biological information of plural subjects and a display displaying biological information of the subject in a display area generated for each subject based on associations between the plural subjects and the plural sensor signals.

BRIEF DESCRIPTION OF THE DRAWINGS

FIG. 3 shows an example of a table indicating correspondence between sensor identification information and subject identification information stored in the above information terminal;

FIGS. 4A and 4B show display examples on a display of the above information terminal;

FIGS. 5A and 5B show display examples on the display of the above information terminal;

DESCRIPTION OF EMBODIMENTS

Figure 1:
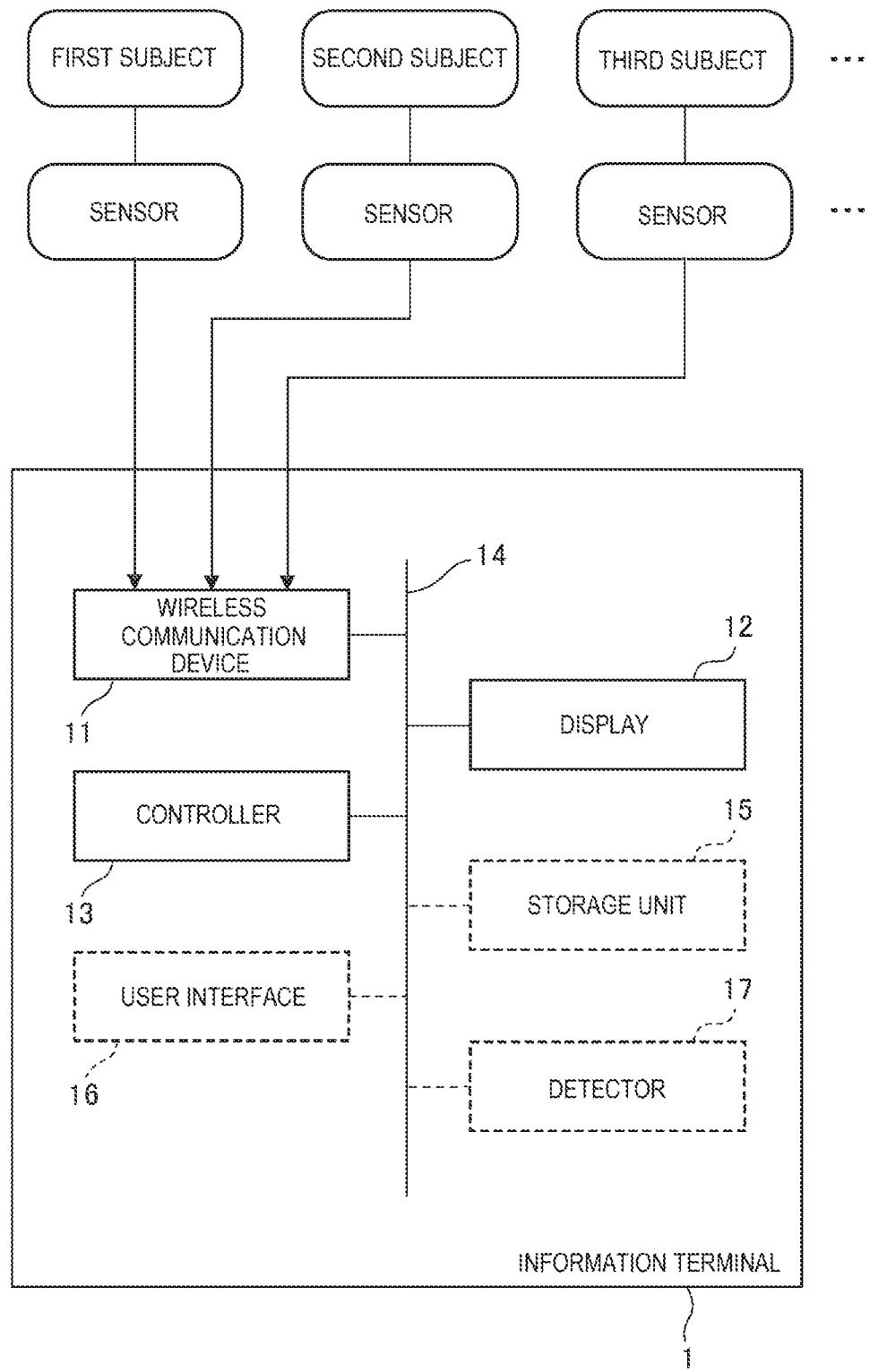
FIG. 1 shows a functional configuration of an information terminal according to an embodiment.

Examples of an embodiment will be explained below in detail with reference to the attached drawings. FIG. 1 shows a functional configuration of an information terminal 1 according to the embodiment.

The information terminal 1 is an apparatus for performing centralized management of biological information acquired from plural subjects. The information terminal 1 forms a biological information management system with at least one sensor attached to each subject.

The sensor has a configuration in which biological information of a subject is detected and a signal corresponding to the biological information is outputted. As biological information, a body temperature, a blood pressure, an electrocardiogram, an electromyogram, brain waves, noninvasive arterial blood saturation (SpO2), concentration of carbon dioxide or oxygen in respiratory gas, a partial pressure and so on can be cited.

The information terminal 1 includes a wireless communication device 11. The wireless communication device 11 includes a communication interface capable of performing wireless communication with the sensors. As such interfaces, communication interfaces conforming to standards such as RFID (Radio Frequency Identification), NFC (Near Field Communication), Bluetooth (trademark) and Wi-Fi can be cited. The wireless communication device 11 receives at least one sensor signal from at least one sensor attached to each subject.

The information terminal 1 includes a display 12. The display 12 is configured to display various types of information. As the display 12, a liquid crystal display, an organic EL display device and the like can be cited.

The information terminal 1 includes a controller 13. The controller 13 includes a processor. The processor is configured to execute at least part of a later-described biological information management method. Functions of the processor may be realized by a general-purpose microprocessor operating in cooperation with a memory, or may be realized by a dedicated integrated circuit such as a microcontroller, FPGA or ASIC.

The information terminal 1 includes a communication bus 14. The wireless communication device 11, the display 12 and the controller 13 can exchange signals and data mutually through the communication bus 14.

Figure 2:
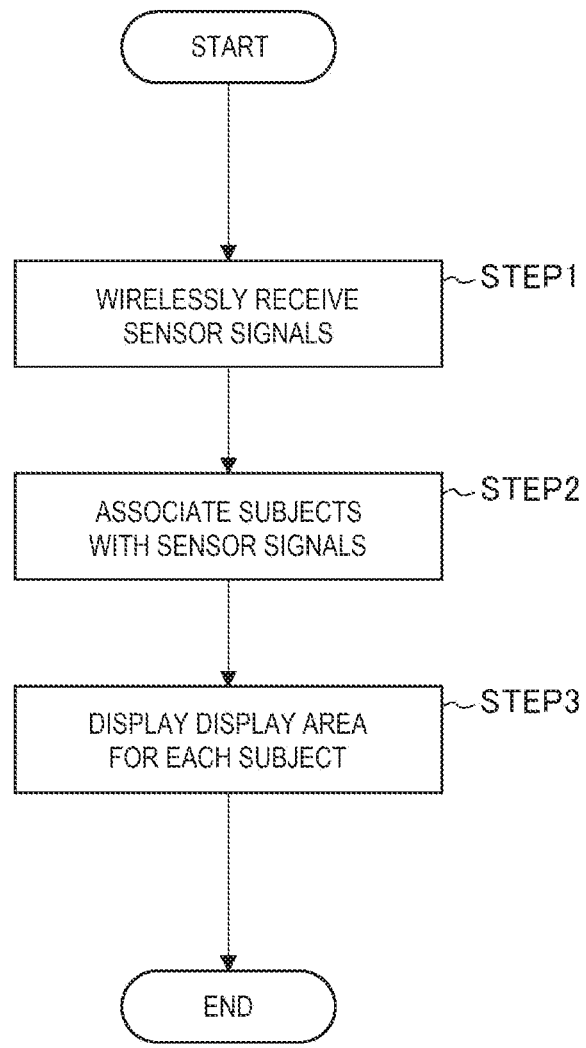
FIG. 2 shows the flow of processing executed by the above information terminal.

FIG. 2 shows an example of a biological information management method performed in a biological information management system configured as described above. Processing executed in the information terminal 1 is performed under control of the controller 13.

First, the wireless communication device 11 wirelessly receives plural sensor signals corresponding to biological information of plural subjects (STEP 1), In the example shown in FIG. 1, sensor signals are received from at least one sensor respectively attached to a first subject, a second subject and a third subject. That is, the number of subjects in the embodiment is three. However, the number of subjects may be two, and may be four or more.

Subsequently, plural subjects are associated with plural sensor signals as shown in FIG. 2 (STEP 2).

For example, the information terminal 1 can include a storage unit 15 as shown in FIG. 1. The storage unit 15 can be connected to the communication bus 14. The storage unit 15 includes a storage in which information for associating plural subjects with plural sensor signals is previously stored. Specifically, a table indicating correspondence between sensor identification information and subject identification information is stored.

FIG. 3 shows an example of the above table. Subject IDs for identifying individual subjects are assigned to respective subjects. In the example, P028 is assigned to the first subject as a subject ID. Similarly, P223 is assigned to the second subject as a subject ID, and P075 is assigned to the third subject as a subject ID.

On the other hand sensor IDs for identifying individual sensors are assigned to respective sensors. In the example, sensor IDs including an initial E indicate sensors for detecting an electrocardiogram. Sensor IDs including an initial S indicate sensors for detecting noninvasive arterial blood saturation (SpO2). Sensor IDs including an initial R indicate sensors for detecting carbon dioxide concentration in respiratory gas. Sensor signals transmitted from respective sensors include information corresponding to sensor IDs.

The controller 13 associates plural subjects with plural sensor signals while referring to the table stored in the storage unit 15. For example, when a sensor signal indicating that the sensor ID is E003 is received, it is found that an electrocardiogram sensor outputting the sensor signal is associated with the first subject the subject ID of which is P028. Similarly, when a sensor signal indicating that the sensor ID is S076 is received, it is found that a SpO2 sensor outputting the sensor signal is also associated with the first subject. Similarly, it is found that the electrocardiogram sensor the sensor ID of which is E098 and the SpO2 sensor the sensor ID of which is S487 are associated with the second subject the subject ID of which is P223.

The order of STEP1 and STEP2 shown in FIG. 2 can be reversed. That is, the association of the sensors ID and the subject Ds may be previously performed in the sensors. For example, the association between the electrocardiogram sensor the sensor ID of which is E003 and the first subject the subject ID of which is P028 can be performed when the electrocardiogram sensor is attached to the first subject. In this case, the sensor signal transmitted from the electrocardiogram sensor includes information corresponding to E003 and P028. In this case, the configuration corresponding to the storage unit 15 can be provided in the sensor.

Subsequently, biological information of the subject is displayed in a display area set for each subject based on association between plural subjects and plural sensor signals (STEP3). FIG. 4A shows an example of display performed on the display 12 of the information terminal 1.

A display area A1 is an area displayed on the display 12 for displaying biological information of the first subject. In the drawing, the display area A1 displays at electrocardiogram waveform corresponding to the sensor signal received from the electrocardiogram sensor attached to the first subject. The display area A1 also displays variation with time of measured values of SpO2 corresponding to the sensor signal received from the SpO2 sensor attached to the first subject.

A display area A2 is an area displayed on the display 12 for displaying biological information of the second subject. In the drawing, the display area A2 displays an electrocardiogram waveform corresponding to the sensor signal received from the electrocardiogram sensor attached to the second subject. The display area A2 also displays variation with time of measured values of SpO2 corresponding to the sensor signal received from the SpO2 sensor attached to the second subject.

That is, each display area is generated based on association between each subject and at least one sensor attached to the subject and displays biological information of the subject acquired through wireless communication.

According to the configuration, the degree of freedom in an arrangement place of the information terminal 1 for performing centralized management of biological information acquired from plural subjects can be increased. Accordingly, the convenience in the centralized management of biological information can be increased.

The information terminal 1 can be carried by a user. In other words, the information terminal 1 is configured to have the size and weight that can be carried by the user. As such information terminals 1, a smart phone, a tablet terminal, a head-mounted display and so on can be cited.

In this case, biological information acquired from plural subjects can be centralized-managed in a place desired by the user. Therefore, the convenience in centralized management of biological information can be increased.

As shown in FIG. 4A, the display 12 can collectively display plural display areas generated for plural subjects.

According to the configuration, browsability of biological information acquired from plural subjects is increased and the convenience in centralized management of biological information can be increased.

In a case where the number of plural sensor signals received from the same subject exceeds a predetermined value, the display area generated for the same subject can be displayed alone on the display 12. For example, a case where the predetermined value is "2" will be explained.

In the example shown in FIG. 4A, the number of sensor signals received for the display area A1 and the number of sensor signals received form the display area A2 are both "2". Therefore, the display area A1 and the display area A2 are collectively displayed. Here, when the carbon-dioxide concentration sensor is further attached to the first subject, the number of sensor signal received for the display area A1 exceeds "2". Therefore, the display area A1 is displayed alone on the display 12 as shown in FIG. 4B. The display area A1 displays variation with time of measured values of carbon dioxide concentration in respiratory gas of the first subject.

That is, in plural display areas to be collectively displayed, the display area in which the number of received sensor signals exceeds the predetermined value is displayed by itself on the display 12. When browsability of biological information of plural subjects takes priority in the case where the number of sensor signals is large, an information amount displayed on the display 12 becomes too much and visibility of information may be reduced instead. According to the embodiment, individual visibility of information displayed in the display area generated for the subject having a larger number of attached sensors takes priority. Such display operation is particularly advantageous in a case where the size of the display 12 is relatively small and the information amount that can be collectively displayed is restricted.

In a case where the number of subjects to be centralized-managed by the information terminal 1 exceeds a predetermined value, an information amount displayed on the display 12 is too much and the visibility of information may be reduced instead when browsability of information of all subjects takes priority. Therefore, a predetermined value can be set concerning the number of subjects collectively displayed on the display 12. For example, the predetermined value can be "2". In this case, as shown in FIG. 4A, the display area for displaying biological information of the third subject is not displayed on the display 12. In a case where individual visibility of the display area A1 relating to the first subject takes priority as shown in FIG. 4B, the display area A2 relating to the second subject is not displayed on the display 12.

In order to secure convenience also in the above case, the information terminal 1 can be provided with a user interface 16 as shown in FIG. 1. The user interface 16 can be connected to the communication bus 14. The user interface 16 is configured to receive given operations from the user. As user interfaces 16, physical switches such as buttons or levers, a touch panel device integrated with the display 12 to allow touch input, a voice recognition device receiving input by voice instructions and a line-of-sight recognition device receiving instructions by line-of-sight input can be cited as examples.

In this case, when the user interface 16 receives a given operation, a display area generated for a subject which has not been originally displayed is displayed on the display 12 as shown in FIGS. 5A and 5B.

For example, when the user interface 16 receives a given operation as shown in FIG. 5A in the state where the display area A1 relating to the first subject and the second display area A2 relating to the second subject are collectively displayed as shown in FIG. 4A, a display area A3 relating to a third subject which has not been originally displayed appears on the display 12 as shown in FIG. 5B.

When the user interface 16 receives a given operation in the state where the display area A1 relating to the first subject is displayed alone as shown in FIG. 4B, at least one of the display area A2 relating to the second subject or the display area A3 relating to the third subject which has not been originally displayed appears on the display 12, though not shown.

In the example, the user interface 16 includes the touch panel device allowing touch input with respect to the display 12. In respective display areas displayed on the display 12 in portrait orientation, plural biological information is arranged in a vertical direction. In this case, the above given operation corresponds to a flick operation or a swipe operation in a horizontal direction. In the example, a vertical direction is an example of a first direction and the horizontal direction is an example of the second direction. It is sufficient that the second direction differs from the arrangement direction of plural biological information.

According to the above configuration, both browsability and visibility of plural biological information acquired from plural subjects can be secured in good condition. Therefore, particularly in the case where the display areas displayed on the display 12 are switched by the flick operation or the swipe operation using the touch panel device, intuitive operation can be realized while using generic configuration originally possessed by the information terminal 1.

Figure 6A:
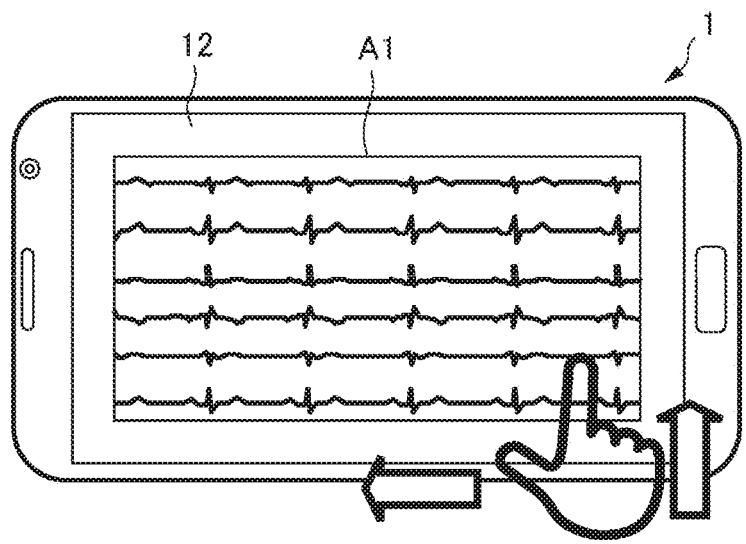
FIGS. 6A and 6B show display examples on the display of the above information terminal.

In the example shown in FIG. 6A, the display area A1 relating to the first subject is displayed alone on the display 12 in landscape orientation. In the display area A1, plural inductive waveforms in an electrocardiogram are displayed so that a time axis is taken along the horizontal direction.

Figure 6B:
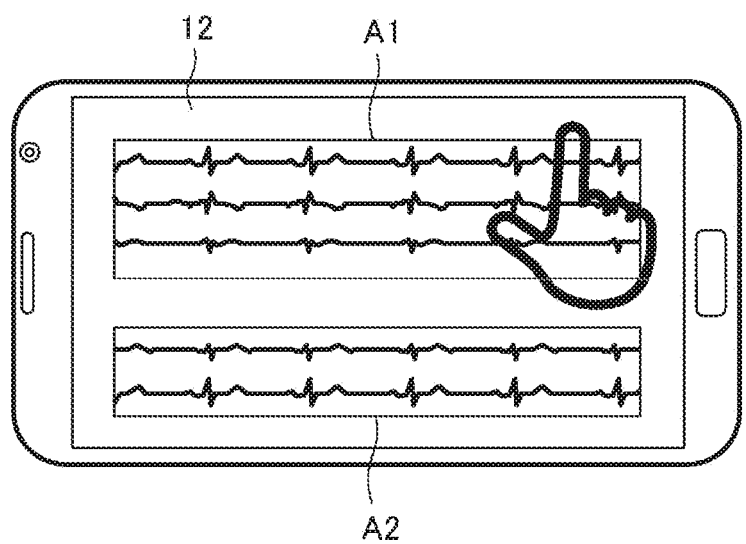

Also in the example, when the user interface 16 receives a given operation, the display area A2 relating to the second subject which has not been originally displayed appears on the display 12 as shown in FIG. 6B.

Specifically, the given operation corresponds to a flick operation or a swipe operation in the vertical direction. In the example, the horizontal direction is an example of a first direction and the vertical direction is an example of a second direction. It is sufficient that the second direction differs from the direction of the time axis.

When the user interface 16 receives the flick operation or the swipe operation in the horizontal direction in the state shown in FIG. 6A, biological information displayed inside the display area A1 is scrolled in the horizontal direction. According to the operation, the user can easily recognize a state at a desired time in biological information. Accordingly, convenience in centralized management of biological information is improved.

Figure 7A:
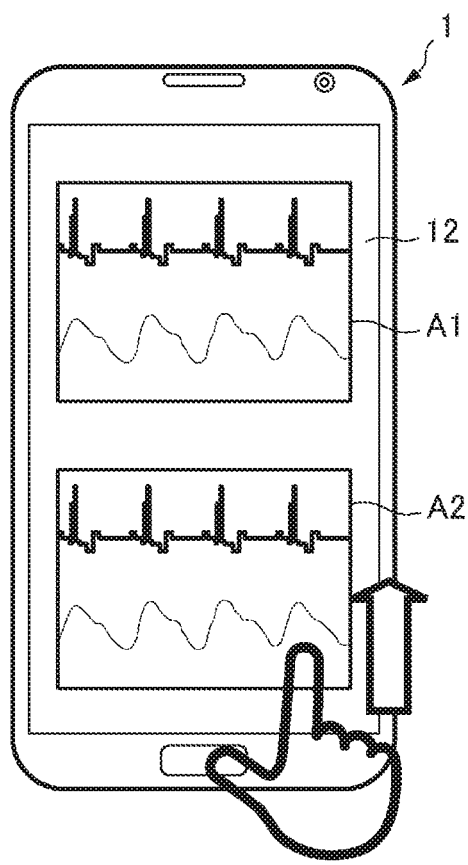
FIGS. 7A and 7B show display examples on the display of the above information terminal.

The same operation of the display can be applied also to the example shown in FIG. 4A. The method can be adopted instead of the switching operation to the display state shown in FIG. 4B. FIG. 7A shows the same display state as FIG. 4A. That is, the display area A1 relating to the first subject and the display area A2 relating to the second subject are collectively displayed on the display 12. In the example, the carbon-dioxide concentration sensor is assumed to be attached to the second subject in addition to the electrocardiogram sensor and the SpO2 sensor.

Figure 7B:
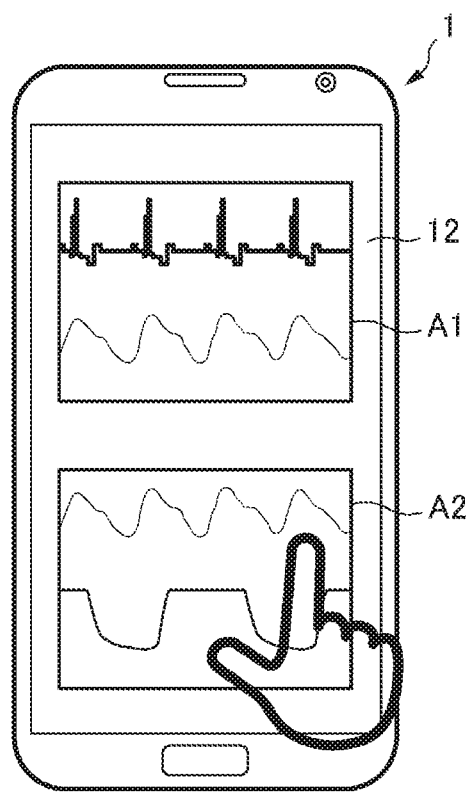

As shown in FIG. 7A, a waveform indicating variation with time of measured values of carbon dioxide concentration is not displayed in the display area A2. When the flick operation or the swipe operation in the vertical direction is inputted to the display area A2 of the display 12 in this state, biological information displayed in the display area A2 is scrolled in the vertical direction. As a result, the waveform indicating variation with time of carbon dioxide concentration Which has not been originally displayed appears in the display area A2 as shown in FIG. 7B.

According to the configuration, specific biological information relating to a specific subject can be checked only when necessary while maintaining browsability of biological information of plural subjects. Accordingly; convenience in centralized management of biological information is improved.

Also in the case where the display area A1 relating to one subject is displayed alone on the display 12 as shown in FIG. 4B, if there exists biological information not originally displayed in the display area A1, biological information displayed inside the display area A1 is scrolled in the vertical direction when the flick operation or the swipe operation is inputted to the display area A1, As a result, a waveform indicating variation with time of biological information which has not been originally displayed appears in the display area A1.

As shown in FIG. 1, the information terminal 1 can be provided with a detector 17. The detector 17 can be connected to the communication bus 14. The detector 17 can include a well-known configuration in which distances from respective subjects or radio wave intensities from sensors attached to respective subjects are detected.

In this case, a display area displaying biological information of one subject determined to be closest in plural subjects based on a detection result by the detector 17 can be highlighted on the display 12. For example, the subject to which a sensor with the highest intensity of radio waves is attached is determined as the closest subject.

Figure 8A:
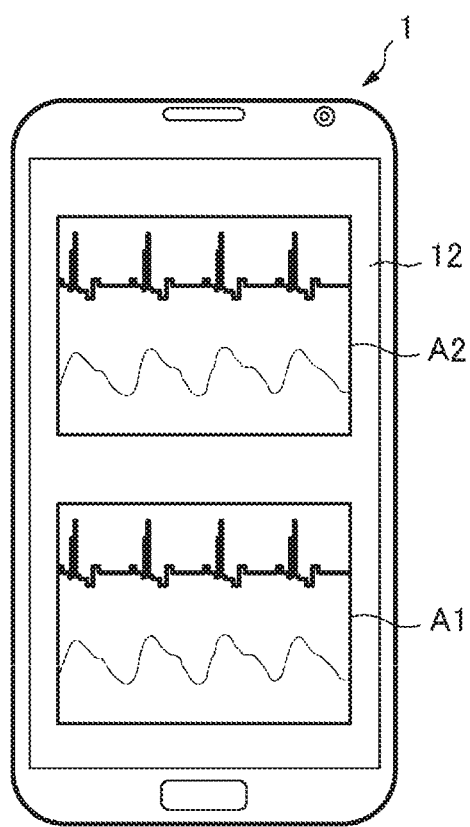
FIGS. 8A and 8B show display examples on the display of the above information terminal.

FIG. 8A shows an example of highlighting. In the example, the second subject is determined to be closest through the detector 17. As a result, the display area A2 relating to the second subject is arranged on the top of the display 12. When the position of the information terminal 1 changes from the state and it is determined that the first subject is the closest subject, the display state of the display 12 is changed to the state shown in FIG. 4A. That is, the display area A1 relating to the first subject is arranged on the top of the display 12.

Figure 8B:
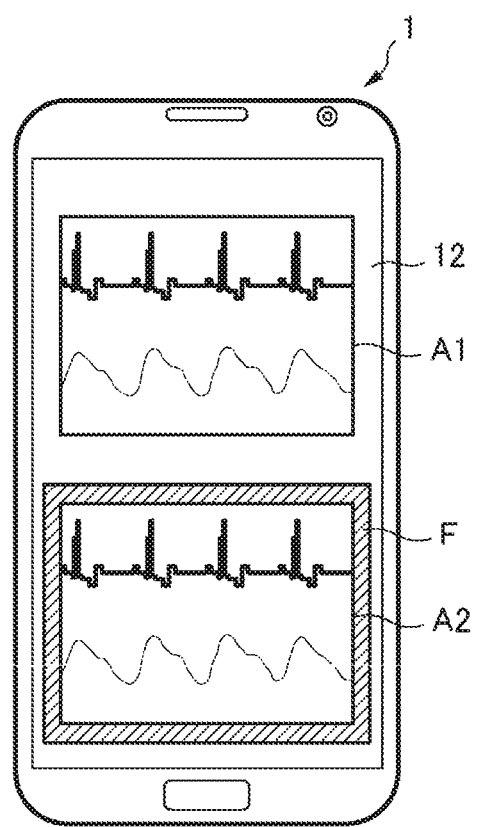

FIG. 8B shows another example of highlighting. Also in the example, the second subject is determined to be closest through the detector 17. As a result, the display area A2 relating to the second subject is displayed with a highlight frame F. When the position of the information terminal 1 changes from the state and it is determined that the third subject is the closest subject, the display area A3 relating to the third subject which has not been originally displayed appears on the display 12 with the highlight frame F. An image added for highlighting is not limited to the highlight frame F but may be suitably selected.

To display the display area relating to one subject determined to be closest alone on the display is also an example of highlighting. In this case, the display state as shown in FIG. 4B can be obtained. Additionally, to gray out or to shade the display areas relating to subjects other than one subject determined to be closest is also an example of highlighting.

It is highly probable that the user intends to check biological information of the closest subject. According to the above configuration, it is possible to make an access to biological information of a subject requiring a check rapidly and easily. As a result, convenience in centralized management of biological information is improved.

The biological information management method is realized by executing a biological information management program by the processor of the information terminal 1. The program may be previously installed in a memory working with the processor as well as may be read out from a storage medium storing the program. Such storage medium may be provided as a portable storage medium such as a SD card or a USB memory as well as may be a storage medium included by a server device to which the information terminal 1 can be connected through a communication network.

The above embodiment is just an exemplification for making the present invention easy to understand. The configurations relating to the above embodiment can be suitably altered and improved within a scope not departing from the gist of the present invention.

As one aspect for achieving the above object, there is proposed an information terminal including a wireless communication device receiving plural sensor signals corresponding to biological information of plural subjects and a display displaying biological information of the subject in a display area generated for each subject based on associations between the plural subjects and the plural sensor signals.

According to the above configuration, the degree of freedom in an arrangement place of the information terminal for performing centralized management of biological information acquired from plural subjects can be increased. Accordingly, convenience in centralized management of biological information can be increased.

As another aspect for achieving the above object, there is proposed a biological information management method executed by a processor in a biological information management system including plural sensors wirelessly transmitting plural sensor signals corresponding to biological information of plural subjects and an information terminal provided with the processor and receiving the plural sensor signals, which includes the steps of associating the plural subjects with the plural sensor signals and displaying display areas generated for respective subjects and displaying biological information of the subjects on a display of the information terminal based on the association.

As further another aspect for achieving the above object, there is proposed a biological information management program allowing the above biological information management method to be executed by an information terminal.

As further another aspect for achieving the above object, there is proposed a computer-readable storage medium storing the above biological information management program.

What is claimed is:

1. An information terminal comprising:
   a wireless communication device receiving plural sensor signals corresponding to biological information of plural subjects;
   a display configured to display biological information of one of the subjects in a display area generated for each subject based on associations between the plural subjects and the plural sensor signals, wherein plural biological information is respectively arranged in plural display areas along a first direction; and
   a user interface receiving a first flick operation or a first swipe operation in a second direction different from the first direction, wherein when the user interface receives the first flick operation or the first swipe operation, a second display area generated for biological information of another subject for which has not been originally displayed is displayed on the display,
   wherein the user interface includes a touch panel device allowing touch input with respect to the display, and wherein
   the display is further configured to display only one of the plural display areas displaying biological information of a same subject or plural display areas of the plural subjects based on a comparison of a number of plural sensor signals received for the same subject to a predetermined value.

2. The information terminal according to claim 1, wherein the display is capable of collectively displaying plural display areas generated for the plural subjects.

3. The information terminal according to claim 2, wherein, when the number of plural sensor signals received for the same subject exceeds the predetermined value, only one of the plural display areas displaying biological information of the same subject is displayed on the display.

4. The information terminal according to claim 1, wherein
   the biological information is displayed in the display area so that a time axis is taken along the first direction.

5. The information terminal according to claim 1, wherein, when the user interface receives a second flick operation or a second swipe operation in the first direction, the biological information of the one of the subjects is scrolled in the first direction within the display area.

6. The information terminal according to claim 1, further comprising:
   a detector configured to detect distances from respective subjects or radio wave intensities from sensors attached to the respective subjects,
   wherein the display area configured to display biological information of one subject closest in the plural subjects is displayed on the display based on a detection result by the detector.

7. The information terminal according to claim 1, further comprising:

a detector configured to detect distances from respective subjects or radio wave intensities from sensors attached to the respective subjects, wherein the display area configured to display biological information of one subject determined to be closest in the plural subjects is highlighted on the display based on a detection result by the detector.

8. The information terminal according to claim 1, further comprising:

a storage unit storing information indicating the associations.

9. The information terminal according to claim 1, wherein information indicating the associations is included in the sensor signals.

10. The information terminal according to claim 1, wherein the information terminal is capable of being carried by a user.

11. The information terminal according to claim 1, wherein the first direction is a vertical direction and the second direction is a horizontal direction.

12. A biological information management method executed by a processor in a biological information management system including plural sensors wirelessly transmitting plural sensor signals corresponding to biological information of plural subjects and an information terminal provided with the processor and receiving the plural sensor signals, the method comprising the steps of:

associating the plural subjects with the plural sensor signals;

displaying display areas generated for respective subjects;

displaying biological information of the plural subjects on a display of the information terminal based on the association, wherein the display comprises a touch panel device allowing touch input with respect to the display;

displaying biological information of a same subject or the biological information of the plural subjects on the display based on a comparison of a number of plural sensor signals received for the same subject to a predetermined value;

receiving a flick operation or a swipe operation via the touch panel device; and when the flick operation or the swipe operation is received, displaying other display areas generated for the biological information of the plural subjects for which have not been originally displayed on the display, wherein the flick operation or the swipe operation is received with touch input with respect to the display, plural biological information is respectively arranged in plural display areas along a first direction, and the flick operation or the swipe operation is in a second direction different from the first direction.

13. A computer-readable storage medium storing a biological information management program configured to cause a processor in a biological information management system including plural sensors wirelessly transmitting plural sensor signals corresponding to biological information of plural subjects and an information terminal provided with the processor and receiving the plural sensor signals, to perform operations comprising:

associating the plural subjects with the plural sensor signals;

displaying display areas generated for respective subjects;

displaying biological information of the plural subjects on a display of the information terminal based on the association, wherein the display comprises a touch panel device allowing touch input with respect to the display;

displaying biological information of a same subject or the biological information of the plural subjects on the display based on a comparison of a number of plural sensor signals received for the same subject to a predetermined value;

receiving a flick operation or a swipe operation via the touch panel device; and when the flick operation or the swipe operation is received, displaying other display areas generated for biological information of the plural subjects for which the display areas have not been originally displayed on the display, wherein the user interface includes a touch panel device allowing touch input with respect to the display, plural biological information is respectively arranged in plural display areas along a first direction, and the flick operation or the swipe operation is in a second direction different from the first direction.

14. An information terminal comprising:

a wireless communication device receiving plural sensor signals corresponding to biological information of plural subjects; and a display configured to display biological information of one of the subjects in a display area generated for each subject based on associations between the plural subjects and the plural sensor signals, wherein plural biological information is respectively arranged in plural display areas along a first direction, wherein the display is further configured to display only one of the plural display areas displaying biological information of a same subject or plural display areas of the plural subjects based on a comparison of a number of plural sensor signals received for the same subject to a predetermined value.

* * * * *